United States Patent

Jackson

Patent Number: 5,615,417
Date of Patent: Apr. 1, 1997

[54] EAR PROTECTOR

[76] Inventor: Claudia D. Jackson, 1446 St. Claude Ave., New Orleans, La. 70177

[21] Appl. No.: 599,156
[22] Filed: Feb. 9, 1996
[51] Int. Cl.$^6$ ............................................. A41D 13/00
[52] U.S. Cl. ............................................................. 2/209
[58] Field of Search ................................ 2/2, 423, 208, 2/209; 132/319

[56] References Cited

U.S. PATENT DOCUMENTS

| | | | |
|---|---|---|---|
| 428,511 | 5/1890 | Moore | 2/209 |
| 2,597,508 | 5/1952 | Majewski | 2/209 |
| 2,712,134 | 7/1955 | Cyr | 2/209 |
| 2,763,869 | 9/1956 | Bogart et al. | 2/174 |
| 2,812,517 | 11/1957 | Bogart et al. | 2/174 |
| 3,452,365 | 7/1969 | Wallace | 2/209 |
| 4,616,643 | 10/1986 | Jung | 128/151 |
| 4,802,245 | 2/1989 | Miano | 2/209 |
| 4,866,249 | 9/1989 | Howard | 219/225 |
| 4,872,219 | 10/1989 | Duncan | 2/209 |
| 4,916,758 | 7/1988 | Jordan-Ross | 2/174 |
| 5,023,954 | 6/1991 | Lyons | 2/174 |

Primary Examiner—C. D. Crowder
Assistant Examiner—Shirra L. Jenkins
Attorney, Agent, or Firm—Millen, White, Zelano, & Branigan, P.C.

[57] ABSTRACT

An ear protector for protecting outer ear structure including the pinna, helix and ear lobe, includes a U-shaped retainer with first and second legs joined by a bight and a shield which is pivoted to the retainer at the bight. The retainer is slipped over the ear with the bight and one leg being behind the ear. The shield is then pivoted down over the ear to sandwich the ear between the retainer and shield. Preferably, the shield is lined with a soft foam on its inside surface and has a layer of heat protecting foil on its outer surface.

10 Claims, 2 Drawing Sheets

EAR PROTECTOR

FIELD OF THE INVENTION

This invention relates to a device for protecting ears. More particularly, the present invention relates to an ear protector for protecting ears from burns accidentally inflicted by straightening combs and curling irons.

BACKGROUND OF THE INVENTION

In order to straighten or curl one's hair using a straightening comb or curling iron, locks of hair are passed through the tines of a hot comb or are rolled around the curling iron. When doing this, it is desirable to get as close to the scalp as possible. When this procedure is done by a skilled hair stylist, it is unusual to burn a patron's ear, but when done at home, women frequently burn their ears. Other than being unattractive, ear burns are not usually serious; but upon occasion, an ear burn can become infected or not heal properly so as to require medical attention and perhaps leave a permanent scar. In any event, ear burns are an injury to be avoided.

The patent literature includes a number of inventions directed to ear protectors which shield ears from curling irons. To the inventor's knowledge, none of these inventions have achieved sufficient commercial significance so as to be widely available, if available at all. For example, in 1929, U.S. Pat. No. 1,697,102 issued to a Lillian Barrington. This ear protector had a particular size and shape. Since there is a wide variety of ear sizes and shapes, this protector requires an enormous variety of configurations for commercial success and requires that ears be sorted into sizes such as is the case for shoes, hats and just about every other item of clothing. A more recent patent, U.S. Pat. No. 5,023,954 which issued on Jun. 18, 1991 to Calvin R. Lyons requires a Velcro®-attached headband to hold ear protectors in place with the position of the ear protectors requiring slidable adjustment on the headband. Ear protectors have been used for other purposes such as to prevent shampoo and other treatment substances from entering the ears. Such protectors are illustrated in patents such as U.S. Pat. Nos. 2,763,869 and 2,812,517 to Bogart, et al. Again, these ear protectors are relatively complex in structure and require some arrangement for adjusting the physical configuration of the protector to accommodate ears of various sizes and shapes.

In view of the aforementioned considerations, there is a need for ear protectors which are especially suitable for women with short hair styles who hot curl their own hair so as to avoid ear burns from hot curling irons, which burns are both embarrassing and unattractive. Such protectors should be easy to use, easy to clean and comfortable to wear. They should also be configured for use by professional hair dressers so as to avoid the occasional burn which might occur at a beauty salon. Since the ear protectors are primarily for personal use and are used over and over again, they need to be easy to clean, lightweight, compact and of ·a durable construction, and should be easily manufacturable in different colors.

SUMMARY OF THE INVENTION

Upon further study of the specification and appended claims, further objects and advantages of this invention will become apparent to those skilled in the art.

It is an object of the present invention to provide a new and improved ear protector, especially suitable for avoiding ear burns when curling or straightening hair using a hot comb or curling iron.

In view of this object and other objects, the present invention is directed to an ear protector for protecting outer ear structure known as the pinna, the ear protector comprising a U-shaped retainer having first and second legs joined by a bight portion, wherein one leg extends in front of the ear and the bight and the other leg extend behind the helix portion of the pinna, with the cartilage of the pinna providing support for stabilizing the retainer. A shield having a length and width sufficient to cover the ear when laid thereover is hinged to the bight of the U-shaped retainer by a hinge which is constructed and arranged to facilitate overlapping of the U-shaped retainer by the shield.

In a further aspect of the invention, the ear protector hinge and shield are unitary and made of plastic with the shield having an inner surface which faces the ear when folded thereover and an outer surface, the inner surface having a layer of soft material, such as a foam, affixed thereto.

In still a further embodiment of the invention, the outer surface of the shield has a layer of metal foil thereon.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION

Figure 1:
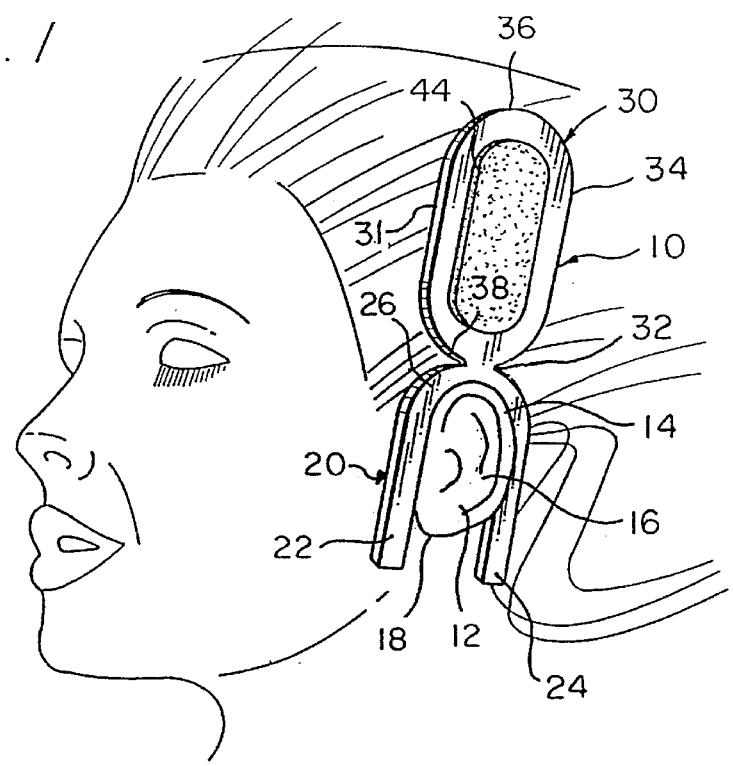
FIG. 1 is a perspective view showing how the ear protector is retained on a person's ear.

Referring now to the drawings, FIG. 1 shows an ear protector 10 configured in accordance with the principles of the present invention for protecting the ear 12 of a person treating their hair with heat by using a curling iron or hot comb. Especially vulnerable to burns by a curling iron or hot comb is the helix 14 of the pinna 16 of the ear 12. The helix 14 is supported by cartilage in the pinna 16 so as to stand out from the person's head. While curling or hot combing their hair, it is desirable to get as close to the scalp as possible. In the area around one's ear, it is not at all unusual to touch the ear with the curling iron and leave a temporary or permanent disfiguring injury.

The ear protector 10 includes a U-shaped retainer 20 comprised of a first leg 22 which fits in front of the ear 12 and a second leg 24 which fits behind the ear and beneath the pinna 16 so as to be overlapped by the helix 14 or outer rim of the ear. The leg 24 is connected to the leg 22 by an arcuate bight portion 26 which also fits behind the pinna 16 so as to be overlain by the helix 14 of the ear. The legs 22 and 24 are long enough to extend past the ear lobe 18 of the ear 12.

A shield 30 is pivoted to the retainer 20 at the bight 26 by a hinge 32. The shield 30 is generally oblong in shape, having straight sides 32 and 34 and arcuate ends 36 and 38.

Figure 2:
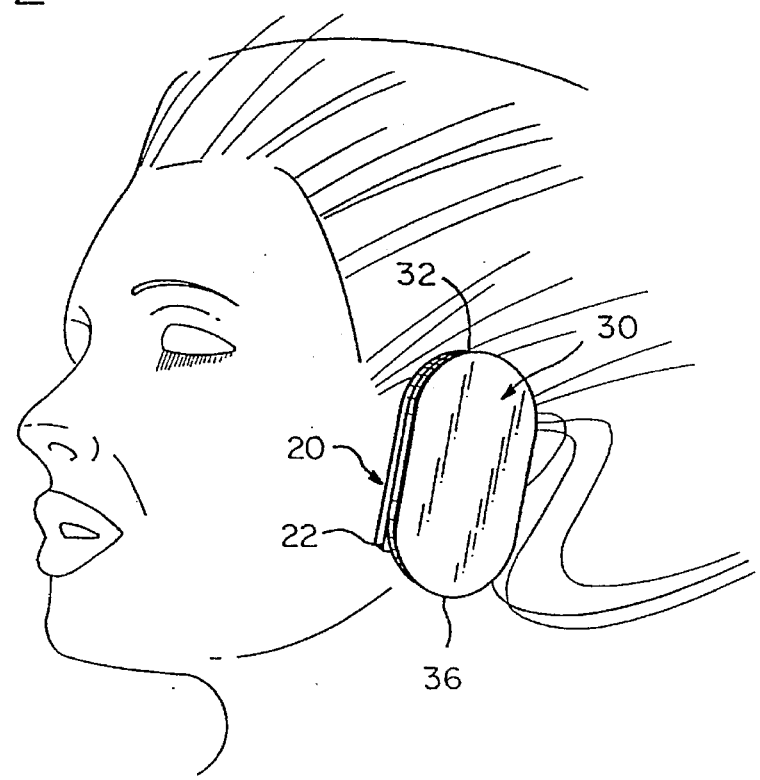
FIG. 2 is a perspective view showing a shield portion of the ear protector overlying the ear of the person using the protector.
Figure 3:
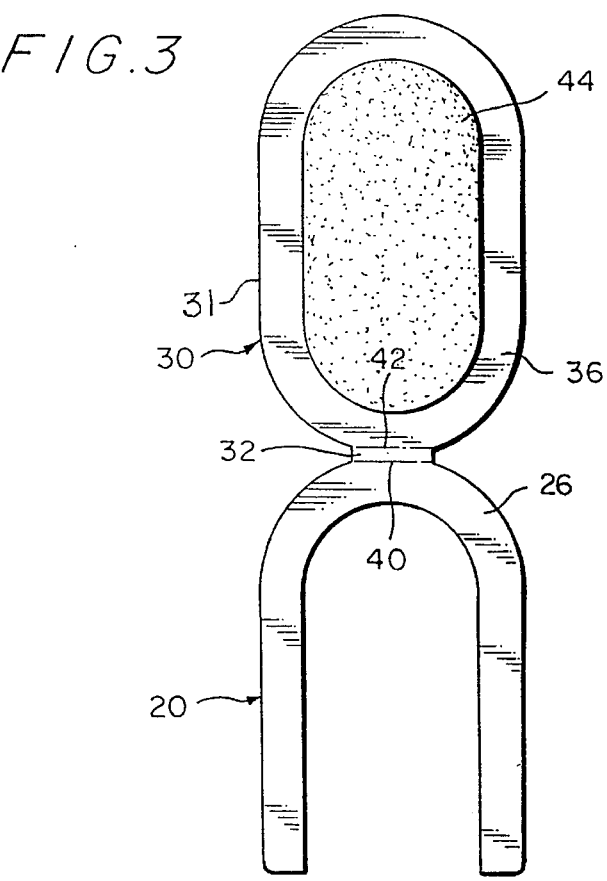
FIG. 3 is a front planar view of the ear protector of FIGS. 1 and 2.
Figure 4:
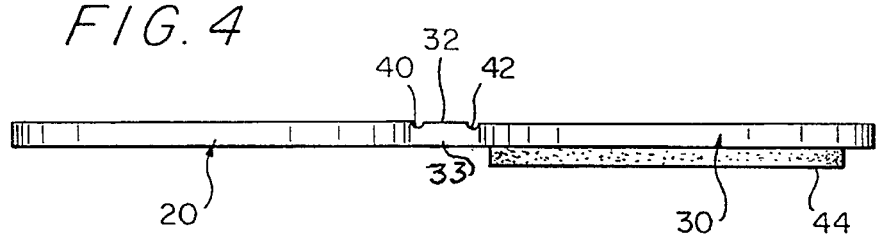
FIG. 4 is a side view of the ear protector of FIG. 3.

In operation, the shield 30 pivots about the hinge 32 and overlies the ear as is seen in FIG. 2. The stiff cartilage of the pinna 16 supports the retainer 22 while the shield 30 clamps the ear 12 between the retainer and shield so that the ear protector 10 is stably mounted on the ear. This frees the person using the hot comb or hot curling iron so that they have both hands free with no fear of burning their ear. In order for the shield 30 to clamp the ear 12, it is preferable that the hinge 32 have a memory in the closed position so that when the ear protector 10 is in its relaxed state, the shield 30 will move to overlie the retainer 20. Consequently, by using the ear protector more attention can be paid to styling their hair which may result in a faster and better job.

Figure 5:
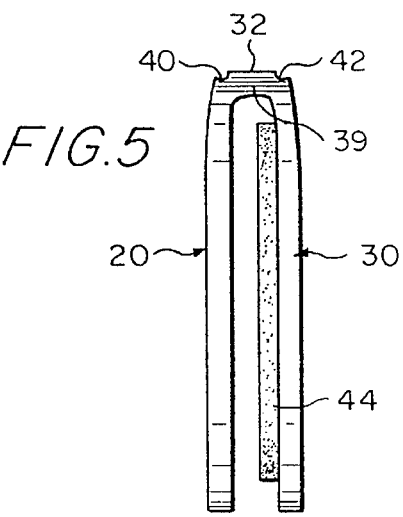
FIG. 5 is a side view showing the ear protector of FIGS. 3 and 4 bent into a U-shape for protecting the ear when mounted as is shown in FIG. 2.
Figure 6:
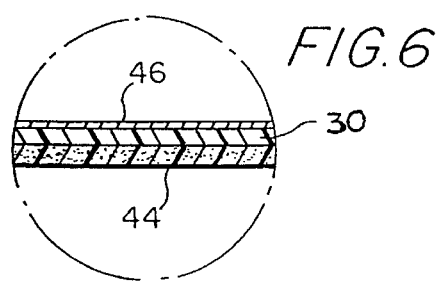
FIG. 6 is an enlarged cross-section of the shield portion of the ear protector showing that it is laminated of foil, plastic and foam.

Referring now to FIGS. 3–6, where a specific embodiment of the invention is shown, it is seen that the hinge 32 is in the form of a bridge 33 which is connected by a first hinge line 40 to the bight 26 of the retainer 20 and is connected by a second hinge line 42 to the shield 30. Preferably, the supporting or rigid structure of the ear protector 10 is of a unitary plastic construction. In order to improve comfort and to minimize the possibility of heat transfer through the ear protector 10, the shield 30 has a layer of soft material such as foam 44 laminated thereto. As is seen in FIG. 6, a layer of foil 46 may overlie the outer surface of the plastic shield 30 so that the plastic shield 30 is sandwiched between the outer metal foil layer 46 and the inner foam layer 44.

Preferably, the memory of the hinge 32 is such that the protector is biased to the FIG. 5 position for clamping automatically over the user's ear. By connecting the retainer 20 to the shield 30 with the bridge 32, the retainer and shield are spaced apart so as to accommodate the thickness of the ear resulting from specifically the convex configuration of the helix 14 (see FIG. 1) of the ear.

From the foregoing description, one skilled in the art can easily ascertain the essential characteristics of this invention, and without departing from the spirit and scope thereof, can make various changes and modifications of the invention to adapt it to various usages and conditions.

What is claimed:

1. An ear protector for protecting outer ear structure including the pinna, helix and ear lobe, the ear protector comprising:

a U-shaped retainer having first and second legs joined by a bight wherein one leg extends in front of the ear and the bight and the other leg extends behind the helix portion of the pinna with the cartilage of the pinna providing support for stabilizing the retainer;

a shield having a length and width sufficient to cover the ear when laid thereover, and a hinge joining the shield to the bight of the U-shaped retainer, the hinge being constructed and arranged to facilitate overlapping of the U-shaped retainer by the shield.

2. The ear protector of claim 1, wherein the shield, hinge and shield are unitary and made of plastic.

3. The ear protector of claim 2, wherein the shield has an inner surface which faces the ear when folded thereover and an outer surface, the inner surface having a layer of soft material affixed thereto.

4. The ear protector of claim 3, wherein the outer surface has a layer of metal foil thereon.

5. The ear protector of claim 4, wherein the soft material is a foam material.

6. The ear protector of claim 3, wherein the soft material is a foam material.

7. The ear protector of claim 1, wherein the hinge is configured to bias the shield to a position overlying the U-shaped retainer.

8. The ear protector of claim 7, wherein the U-shaped retainer, shield and hinge are unitary.

9. The ear protector of claim 8, wherein the ear protector is made of plastic.

10. The ear protector of claim 9, wherein the hinge is a bridge pivoted at one end to the U-shaped retainer and at the other end to the shield to bridge the helix of the ear.

\* \* \* \* \*